(12) United States Patent
Boone et al.

(10) Patent No.: US 11,844,628 B2
(45) Date of Patent: Dec. 19, 2023

(54) METHOD OF FORMING A TRANSFORMER ASSEMBLY

(71) Applicant: Medtronic, Inc., Minneapolis, MN (US)

(72) Inventors: Mark R. Boone, Gilbert, AZ (US); Mark S. Ricotta, Tempe, AZ (US); Mohsen Askarinya, Chandler, AZ (US); Lejun Wang, San Diego, CA (US)

(73) Assignee: Medtronic, Inc., Minneapolis, MN (US)

( * ) Notice: Subject to any disclaimer, the term of this patent is extended or adjusted under 35 U.S.C. 154(b) by 534 days.

(21) Appl. No.: 16/943,709

(22) Filed: Jul. 30, 2020

(65) Prior Publication Data

US 2020/0352508 A1    Nov. 12, 2020

Related U.S. Application Data

(60) Continuation of application No. 15/378,222, filed on Dec. 14, 2016, now abandoned, which is a division of
(Continued)

(51) Int. Cl.
*A61B 5/00* (2006.01)
*A61N 1/05* (2006.01)
(Continued)

(52) U.S. Cl.
CPC ............... *A61B 5/686* (2013.01); *A61B 5/29* (2021.01); *A61N 1/025* (2013.01); *A61N 1/0587* (2013.01); *A61N 1/3758* (2013.01); *A61N 1/3956* (2013.01); *H01F 27/24* (2013.01); *H01F 27/2804* (2013.01); *H01F 27/29* (2013.01); *H01F 41/0206* (2013.01);
(Continued)

(58) Field of Classification Search
CPC ...... A61B 2560/0214; A61B 2562/125; A61B 5/283; A61B 5/686; A61N 1/025; A61N 1/0587; A61N 1/3758; A61N 1/3956; H01F 2027/2809; H01F 2027/2819; H01F 27/24; H01F 27/2804
See application file for complete search history.

(56) References Cited

U.S. PATENT DOCUMENTS

| | | |
|---|---|---|
| 3,243,752 A | 3/1966 | Lawrence |
| 3,672,046 A | 6/1972 | Storey et al. |

(Continued)

FOREIGN PATENT DOCUMENTS

| | | |
|---|---|---|
| EP | 1796790 | 6/2007 |
| EP | 1620171 | 11/2010 |
| WO | 1999/015861 | 4/1999 |

*Primary Examiner* — Minh N Trinh
(74) *Attorney, Agent, or Firm* — Mueting Raasch Group

(57) ABSTRACT

The present disclosure provides methods and techniques associated with a planar transformer for an apparatus. The planar transformers include a substrate carrying electronic components and a continuous core that is formed by distributing the encapsulant material uniformly around the substrate unit to define a consistent cross-sectional area for the magnetic path. The electronic components include primary windings and secondary windings associated with the transformer. In some embodiments, the encapsulant material is molded to seals air gaps to the substrate unit.

17 Claims, 8 Drawing Sheets

Related U.S. Application Data application No. 13/798,776, filed on Mar. 13, 2013, now abandoned.

(51) Int. Cl.
  *A61N 1/375* (2006.01)
  *H01F 41/02* (2006.01)
  *A61B 5/29* (2021.01)
  *A61N 1/02* (2006.01)
  *A61N 1/39* (2006.01)
  *H01F 27/24* (2006.01)
  *H01F 27/28* (2006.01)
  *H01F 27/29* (2006.01)

(52) U.S. Cl.
  CPC .. *H01F 41/0246* (2013.01); *A61B 2560/0214* (2013.01); *A61B 2562/125* (2013.01)

(56) References Cited

U.S. PATENT DOCUMENTS

| | | | |
|---|---|---|---|
| 4,128,527 A | 12/1978 | Kinjo et al. |
| 4,387,311 A | 6/1983 | Kobayashi et al. |
| 4,879,055 A | 11/1989 | Sezaki et al. |
| 5,010,313 A | 4/1991 | Kaneko et al. |
| 5,160,447 A | 11/1992 | Ishikawa et al. |
| 5,345,670 A | 9/1994 | Pitzele et al. |
| 5,804,952 A | 9/1998 | Chen |
| 5,853,771 A | 12/1998 | Matsumoto |
| 5,891,384 A | 4/1999 | Miyajima |
| 6,080,354 A | 6/2000 | Miyajima |
| 6,106,259 A | 8/2000 | Lee et al. |
| 6,190,589 B1 | 2/2001 | Bryant et al. |
| 6,267,577 B1 | 7/2001 | Nishi et al. |
| 6,477,414 B1 | 11/2002 | Silvian |
| 6,478,562 B1 | 11/2002 | Miyajima |
| 6,498,055 B2 | 12/2002 | Fukuda et al. |
| 6,594,157 B2 | 7/2003 | Yoshida et al. |
| 6,682,958 B2 | 1/2004 | Matsumoto |
| 6,770,236 B2 | 8/2004 | Miyajima |
| 6,773,247 B1 | 8/2004 | Osada et al. |
| 6,792,667 B2 | 9/2004 | Roy et al. |
| 6,906,608 B2 | 6/2005 | Fujiwara et al. |
| 6,927,661 B2 | 8/2005 | He et al. |
| 6,927,663 B2 | 8/2005 | Iverson et al. |
| 6,980,078 B2 | 12/2005 | Rouser |
| 6,995,643 B2 | 2/2006 | Fujiwara et al. |
| 7,060,350 B2 | 6/2006 | Takaya et al. |
| 7,106,163 B2 | 9/2006 | Jin et al. |
| 7,167,074 B2 | 1/2007 | Fenner et al. |
| 7,285,235 B2 | 10/2007 | Rapacki et al. |
| 7,799,615 B2 | 9/2010 | Vinciarelli et al. |
| 7,821,373 B2 | 10/2010 | Cheng et al. |
| 7,821,374 B2 | 10/2010 | Harrison et al. |
| 7,915,991 B2 | 3/2011 | Waffenschmidt et al. |
| 8,154,118 B2 | 4/2012 | Kanazawa et al. |
| 8,361,841 B2 | 1/2013 | Lee et al. |
| 8,427,267 B1 | 4/2013 | Vinciarelli |
| 8,427,269 B1 | 4/2013 | Vinciarelli et al. |
| 8,647,110 B2 | 2/2014 | Choi et al. |
| 8,824,161 B2 | 9/2014 | Askarinya et al. |
| 8,830,693 B2 | 9/2014 | Boone |
| 8,874,214 B2 | 10/2014 | Carey et al. |
| 9,628,043 B2 | 4/2017 | Meyer |
| 9,633,772 B2 | 4/2017 | Turnbull et al. |
| 2013/0207767 A1 | 8/2013 | Worthington |
| 2013/0334680 A1 | 12/2013 | Boone et al. |
| 2020/0352508 A1* | 11/2020 | Boone ................. H01F 41/0206 |

* cited by examiner

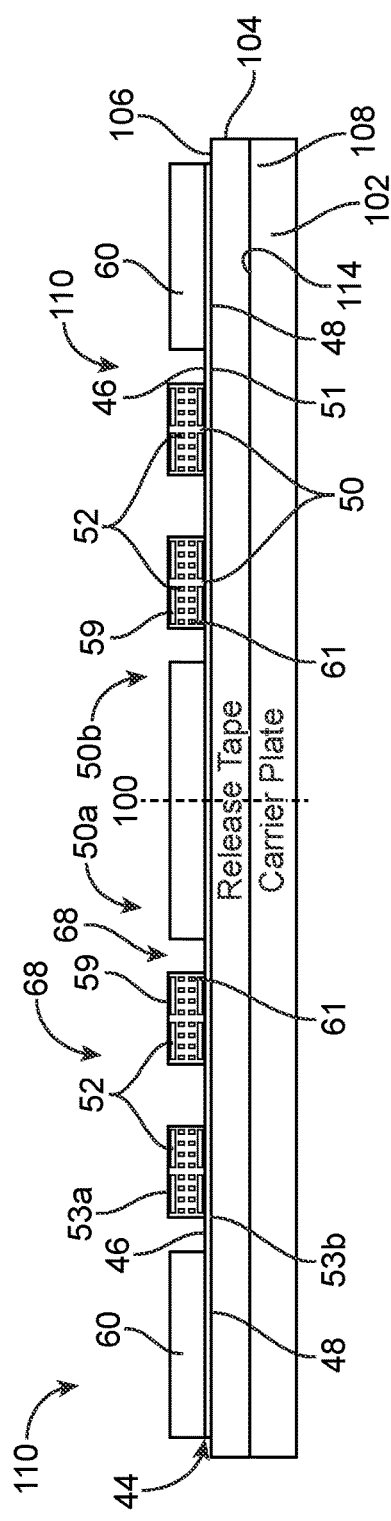
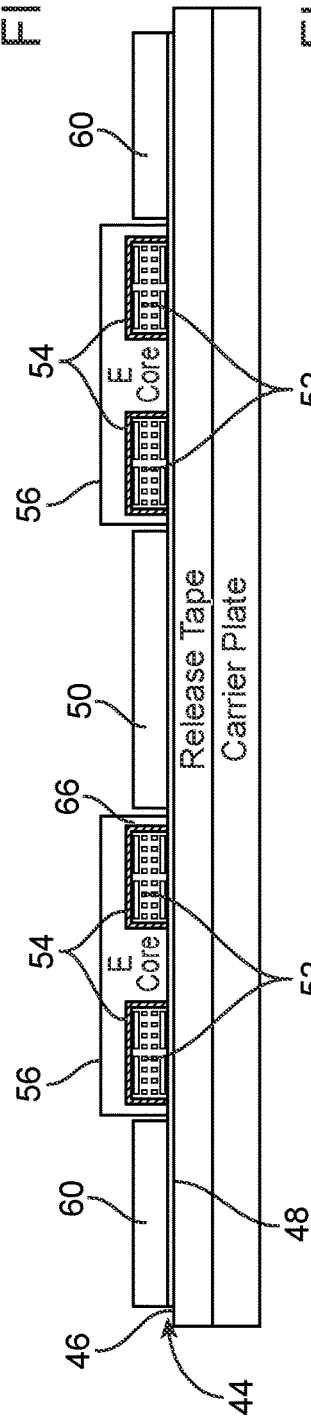
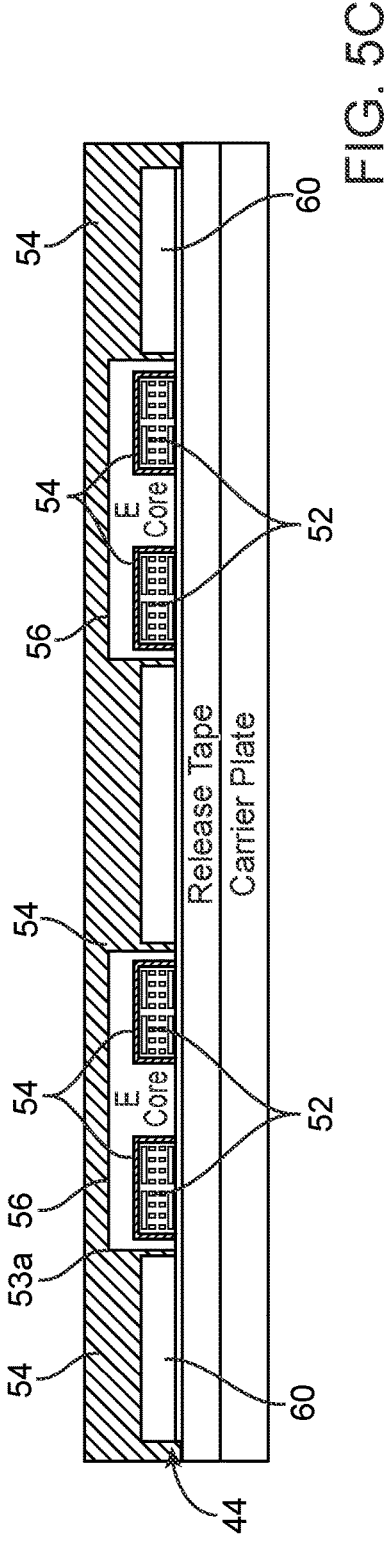
FIG. 5A
FIG. 5B
FIG. 5C

METHOD OF FORMING A TRANSFORMER ASSEMBLY

This application is a continuation of U.S. patent application Ser. No. 15/378,222, filed Dec. 14, 2016, now abandoned, and which is a divisional of U.S. patent application Ser. No. 13/798,776, filed Mar. 13, 2013, now abandoned, which are incorporated herein by reference in their entireties.

FIELD

The present disclosure generally relates to an implantable medical device, and more particularly to transformer assemblies incorporated into the medical device and associated methods for making the transformer assemblies.

BACKGROUND

An implantable medical device (IMD) such as an implantable cardioverter defibrillator (ICD) may be used to deliver shock therapy to a patient's heart in order to perform therapies such as defibrillation and cardioversion. Some ICDs may also provide several different pacing therapies, including such therapies as cardiac resynchronization, depending upon the needs of the user or patient and the medical condition of the patient's heart. For convenience, all types of implantable medical devices will be referred to herein as IMDs, it being understood that the term, unless otherwise indicated, is inclusive of an implantable device capable of administering a cardiac therapy.

In IMDs that deliver defibrillation or cardioversion therapies, it is necessary to develop high voltages, perhaps 750 volts or more, within the IMD in order to administer a sufficient shock to a patient to correct an arrhythmia or a fibrillation, particularly a ventricular fibrillation. To generate such high voltages, a battery and capacitors (usually two) may be used. Preferably, the capacitors are fully charged before defibrillation or cardioversion therapies are delivered. In some configurations, flyback and non-flyback transformers are employed to incrementally charge the defibrillation capacitors prior to therapy delivery. Once the capacitors are charged, the defibrillation or cardioversion therapy is delivered via insulated gate bipolar transistors or other suitable semiconductor switches that are switched on and off to apply charge stored in the capacitors in biphasic pulse waveform to the heart.

Because IMDs are implanted subcutaneously, it is preferable that the IMD is sized as small as possible to reduce any discomfort that the patient may experience post-implantation. Conventionally, however, some of the electronic components that are housed within the IMD are relatively large. For example, transformers are used which have coil and core members that are physically separate from other IMD components. Although these conventional transformers have been reliable, they occupy a considerable amount of space within the IMD.

Accordingly, it remains desirable to provide a method and apparatus for decreasing the size of a transformer for use in an implantable medical device, while maintaining its reliability.

SUMMARY

The present disclosure is directed to an IMD having a hermetically sealed chamber defined by a hermetically sealed housing. Contained within the housing is a power source, a capacitor bank for storing a charge from the power source, and electronic circuitry coupled to the power source and the capacitor bank for charging the capacitor bank through a transformer and for discharging the capacitor-bank charge into selected body tissue.

In an embodiment, techniques are described for making transformer assemblies that are miniaturized sufficiently to fit within small spaces of the housing cavity. The transformer assemblies are provided having a substrate unit that is sandwiched between a pair of cores including an upper and a lower core, both of which may be comprised of a magnetic material. In one embodiment, a transformer assembly includes a substrate unit having electronic components arranged therein. The electronic components arranged in the substrate unit may include primary and secondary windings. A first of the pair of cores, for example, the upper core, is disposed on a top surface of the substrate unit. A second of the pair of cores, for example the lower core, is disposed on a bottom surface of the substrate unit. The transformer further includes an encapsulant material that is dispensed over the upper core and within the gaps between the upper core and the electronic components of the substrate unit. The encapsulant material functions to couple and permanently position the upper core to the top surface. Similarly, the lower core may be permanently positioned on the bottom surface with encapsulant material, while in other embodiments, an adhesive material may be applied to affix the lower core to the substrate unit. In an embodiment, the encapsulant material is formed to expose a surface of the upper and/or lower cores, such surface being parallel to the top surface of the substrate unit.

In a second embodiment, a transformer assembly includes a substrate unit having electronic components and including primary and secondary windings embedded within the substrate unit. The substrate unit may be fully (or substantially) encapsulated by a core that includes an upper core and a lower core. The upper and lower cores may be assembled to eliminate an air gap therebetween. For example, the upper and lower cores may be formed in a molding process from a liquefied encapsulant material that is dispensed to encapsulate the substrate unit.

According to an embodiment of the disclosure, a method for forming a transformer assembly is disclosed. In accordance with the method, a substrate having a plurality of substrate units is provided with each of the substrate units including electronic components. In an embodiment, the electronic components include primary and secondary windings associated with a transformer. The substrate is mounted to a first surface of an adhesive material and a carrier plate is mounted to a second surface of the adhesive material. An upper core is placed over each of the substrate units. An encapsulation of the assembly including the substrate and the upper core is performed by molding to continuously encapsulate the portion of the assembly adhered to the first surface of the adhesive material. In an embodiment, molding includes dispensing an encapsulant material between the air gaps formed by the electronic component and the upper core of each of the substrate units. The substrate is subsequently detached from the adhesive material and a lower core is bonded to each of the substrate units. In an embodiment, the plurality of substrate units are separated into individual units.

In another embodiment, a method for manufacturing a transformer assembly includes encapsulating a substrate unit with an encapsulant material. The substrate unit includes electronics and primary and secondary windings for the transformer. The encapsulant material is formed as a unitary/ continuous member to define a homogeneous core of the transformer, with the windings and/or electronics being embedded within the core. In one embodiment, the core may be formed by distributing the encapsulant material uniformly around the windings to define a consistent cross-sectional area. The encapsulant material may include a polymer bonded magnetic compound.

BRIEF DESCRIPTION

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 5A to 5E depict cross-sectional views of a transformer assembly such as that shown in any one of FIGS. 3A and 3B associated with a method for fabrication of the transformers;

DETAILED DESCRIPTION

The following detailed description is illustrative in nature and is not intended to limit the embodiments of the invention or the application and uses of such embodiments. Furthermore, there is no intention to be bound by any expressed or implied theory presented in the preceding technical field, background, brief summary or the following detailed description.

In the present disclosure, the inventors have disclosed device assemblies and methods for construction associated with transformers. The transformer is one of the constituent electrical components of an implantable medical device and is utilized to convert low battery voltage into a high voltage that is sufficient to charge capacitors that are used to deliver an electrical stimulating therapy. Conventional transformers are built by winding a wire onto a toroid magnetic core. Due to the relatively small size, some of the winding process is manual, which results in significant cost and performance variability. The inventors have observed that the conventional transformer is generally the largest and tallest component in relation to other electrical components of the implantable medical device. The inventors have also observed that the rigidity and fragility of conventional discrete cores creates challenges in reducing the dimensions of the transformer. In accordance with embodiments of the present disclosure, processing techniques and/or materials are described that provide the ability to achieve transformer packages with desired dimensions that may be smaller than those that are achievable with the conventional discrete cores.

Figure 1:
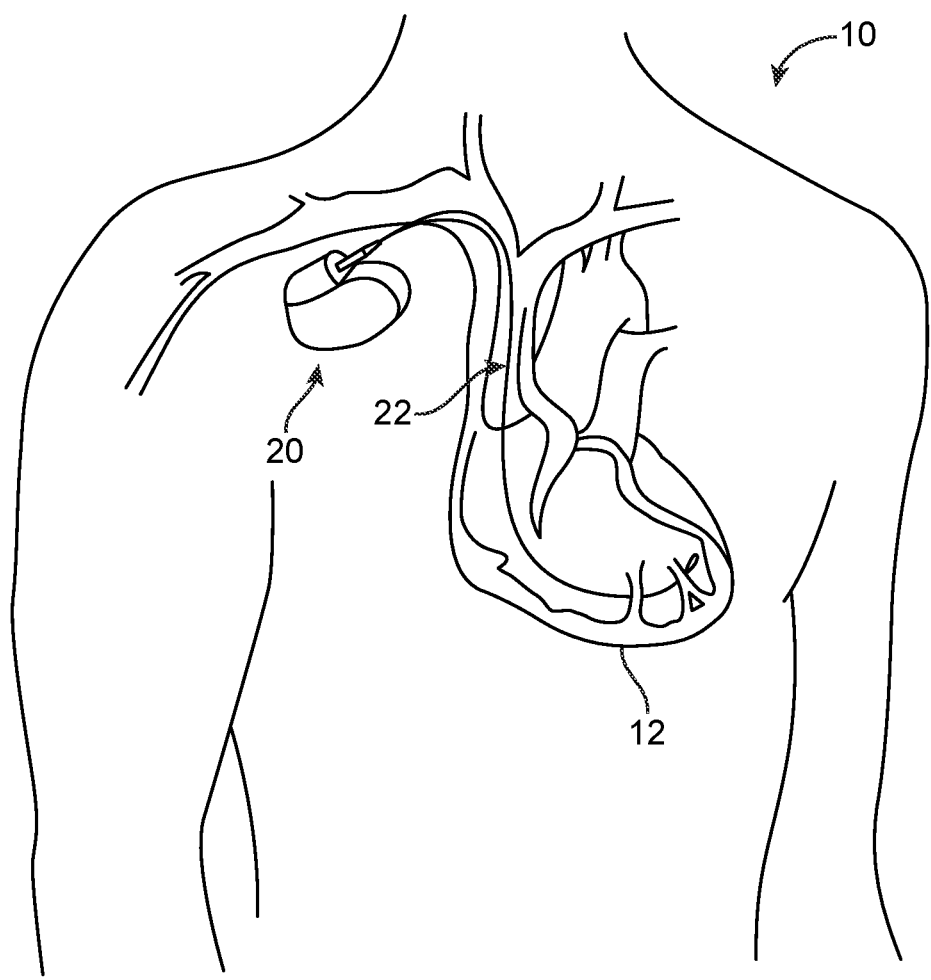
FIG. 1 illustrates an implantable system in accordance with one exemplary embodiment.

FIG. 1 illustrates an implantable system in accordance with one exemplary embodiment of the disclosure. An implantable medical device (IMD) 20 is implanted in a body 10 near a heart 12. IMD 20 includes circuitry, a battery and other components that are contained within a hermetically sealed, biologically inert outer canister or housing that may be conductive so as to serve as a pace/sense electrode in the pacing/sensing circuit. One or more leads, collectively identified with reference numeral 22, electrically couple to the IMD 20 and extend into the heart 12. In the case where device 20 is a pacemaker, leads 22 are pacing and sensing leads to sense electrical signals attendant to the depolarization and repolarization of the heart 12 and provide pacing pulses in the vicinity of the distal ends thereof. One or more exposed conductive pace/sense electrode(s) for sensing electrical cardiac signals or delivering electrical pacing pulses to the heart 12 are disposed at or near the distal ends of the leads 22. The leads 22 may be implanted with their distal ends situated in the atrium and/or ventricles of the heart 12 or elsewhere in cardiac blood vessels in operative relation with a heart chamber. The leads 22 can also carry other sensors for sensing cardiac physiologic data, e.g. pressure, temperature, impedance, pH, blood gas, acceleration, etc.

IMD 20 may also be a pacemaker/cardioverter/defibrillator (PCD) corresponding to any of the various commercially-available implantable PCDs. Those and other alternative implantable devices may be employed using the present disclosure in that such devices may employ or be modified with circuitry and/or systems according to the present disclosure. Examples of such alternative devices of IMD 20 may be an implantable nerve stimulator or muscle stimulator. In fact, the present disclosure is believed to find wide application in any form of an electrical device, and is further believed to be particularly advantageous where low power consumption is desired, particularly in battery powered devices.

In general, IMD 20 includes a hermetically-sealed enclosure that includes a power source and circuitry to control therapy delivery to heart 12. The circuitry may be implemented in discrete logic and/or may include a microcomputer-based system with A/D conversion.

Figure 2:
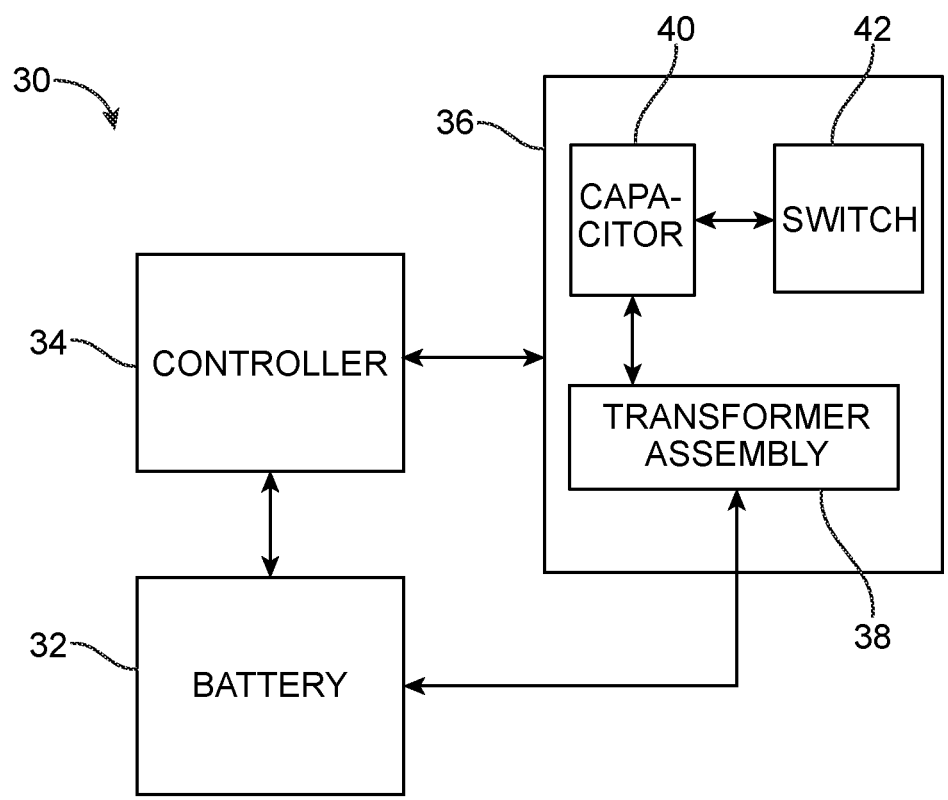
FIG. 2 depicts a simplified block diagram of exemplary circuitry 30 that may be housed within the IMD 20.

FIG. 2 provides a simplified block diagram of exemplary circuitry 30 that may be housed within the IMD 20 and is configured to produce pulses that are used to pace the heart; i.e., cause a depolarization of the heart tissue or issue a defibrillation pulse to shock the heart from arrhythmia to a normal heart beat. Circuitry 30 is shown to include a power source 32 electrically coupled to a controller 34 and a shocking circuit 36. Although circuitry 30 depicts three components, it will be appreciated that fewer or more components may be employed. Power source 32 is configured to provide operating power to controller 34 and shocking circuit 36 and is preferably capable of operating at low current drains over a long duration and at high current pulses when shock delivery to patient 10 is required. Any one of numerous types of appropriate batteries may be used, such as, for example lithium/silver vanadium oxide batteries.

Controller 34 controls the delivery of energy through lead 22 (shown in FIG. 1). Controller 34 is preferably configured to determine when, where, and for what duration the energy may be delivered. In this regard, any one of numerous types of suitable control circuitry, such as microprocessors; or circuitry including memory, logic and timing circuitry; and I/O circuitry, may be employed.

Shocking circuit 36 is configured to generate low or high energy shocking pulses and to deliver the shocking pulses to patient 10 in response to control signals from controller 34. In this regard, shocking circuit 36 includes a transformer assembly 38 that is coupled to at least one capacitor 40, which is in turn coupled to a delivery switch 42. Transformer assembly 38 is configured to operate according to the principles of a flyback inductor, and thus, receives voltage from power source 32 to be converted to an appropriate voltage to be used by shocking circuit 36. The converted voltage is stored in capacitor 40, or any other suitable energy storage device, until the shocking pulse is ready to be delivered. When ready, delivery switch 42 is switched from an off position to an on position thereby routing the shocking pulse to the appropriate leads.

Figure 3A:
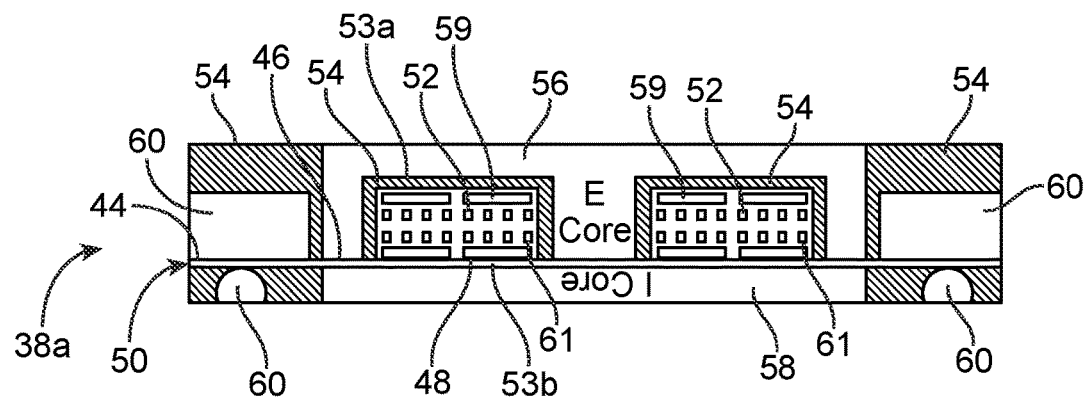
FIG. 3A illustrates a cross-sectional view of a transformer assembly in accordance with an embodiment.

Referring now to FIG. 3A, a cross-sectional view of a transformer assembly 38a in accordance with an embodiment of the disclosure is disclosed. The transformer assembly 38a is shown having a substrate unit 50 and an upper magnetic core 56 disposed over an exterior surface of the substrate unit 50. By way of illustration, the portion of the exterior surface to which the upper magnetic core 56 will be referred to as a top surface 53a. An encapsulant material 54 is dispensed over exterior surfaces of the upper magnetic core 56 and the substrate unit 50 for encapsulation of both the upper magnetic core 56 and substrate unit 50. In an embodiment, the encapsulant material 54 is further dispensed between one or more gaps formed between the substrate unit 50 and the upper magnetic core 56 to eliminate the air gaps therebetween and form an air tight seal. The encapsulant material 54 is formed to expose a surface of the upper magnetic core 56 that is parallel to the top surface of the substrate unit 50. The transformer assembly 38a further includes a lower magnetic core 58 that is bonded to an exterior surface of the substrate unit 50. For ease of discussion, the portion of the exterior surface to which the lower magnetic core 58 is bonded will be referred to as a bottom surface 53b.

The substrate unit 50 includes one or more electronic components 52 that may be partially or fully embedded into the substrate unit 50. The electronic components 52 may include a set of primary windings 59 and secondary windings 61. In one configuration, the primary windings 59 are disposed in an overlapping relation to the secondary windings 61. In another embodiment, the primary windings 59 may be configured in a non-overlapping relation to the secondary windings 61. A pair of terminal connectors 60 is provided for coupling to the primary windings 59 and the secondary windings 61, respectively. The terminal connectors 60 may be formed at least partially on the bottom (and/or top) surface 53a-b of the substrate unit 50 as the external terminals for connecting the transformer assembly 38a to other components of the IMD. As such, the terminal connectors 60 are exposed to facilitate the coupling of the transformer assembly 38a to other components of the IMD 20. For example, the primary windings 59 may be coupled to the battery (FIG. 2) and the secondary windings 61 may be coupled to the capacitors (FIG. 2).

Figure 3B:
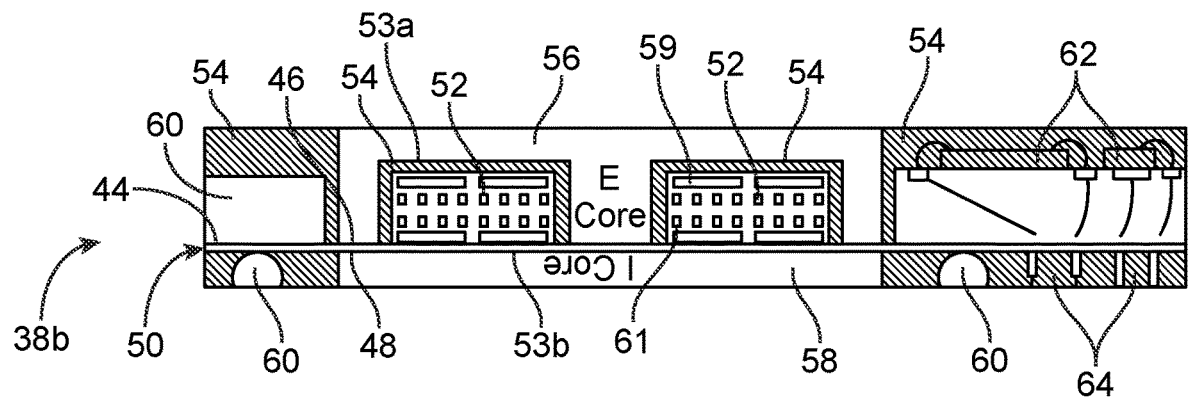
FIG. 3B illustrates a cross-sectional view of an alternative transformer assembly.

FIG. 3B illustrates a cross-sectional view of an alternative transformer assembly 38b. For ease of description, the elements of transformer assembly 38b corresponding to those of transformer assembly 38a are numbered with identical reference designators. The reader is referred to the preceding description of FIG. 3A for a full discussion pertaining to those components.

In the embodiment of FIG. 3B, the transformer assembly 38b includes circuitry 62 that is coupled to the substrate unit 50. In an embodiment, the circuitry 62 may be coupled on the substrate unit 50 adjacent to the upper magnetic core 56 and lower magnetic core 58. The specific components included in circuitry 62 may vary and provide a variety of functionalities. For example, some of the functionality of IMD 20 may be embodied in the components of circuitry 62. The components of circuitry 62 are electrically coupled to one or more terminals 64. The terminals 64 are connectable with additional components of IMD 20.

Figure 4:
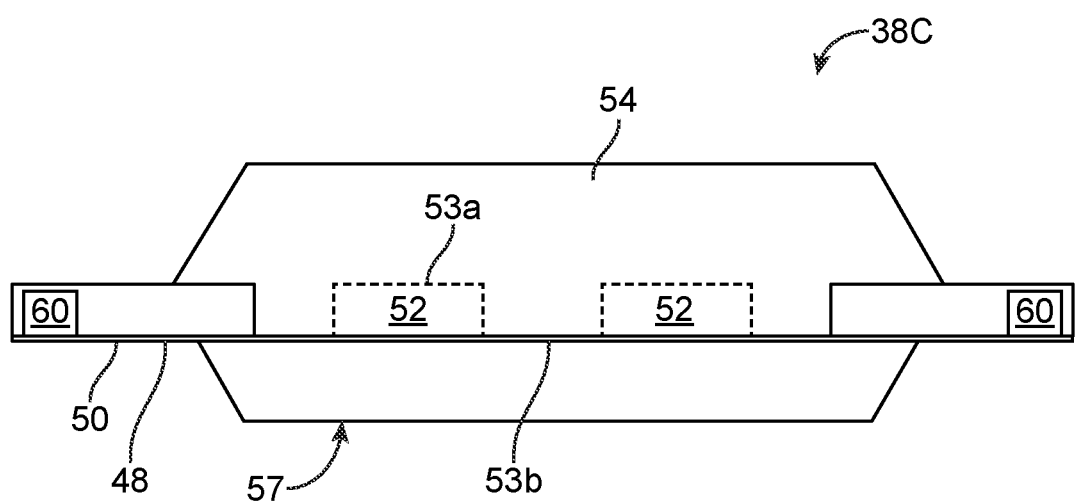
FIG. 4 illustrates a cross-sectional view of another alternative transformer assembly.

FIG. 4 depicts a cross-sectional view of another transformer assembly 38c. Transformer assembly 38c includes a substrate unit 50. A portion of the substrate unit 50 is formed having embedded electronic components 52 that may include a set of primary windings and secondary windings. The substrate unit 50 further includes a pair of terminal connectors 60 that are electrically coupled to the electronic components 52. Among other things, the terminal connectors 60 facilitate coupling of the primary and secondary windings to other components of the IMD 20. For example, the primary windings may be coupled to the battery (FIG. 2) and the secondary windings may be coupled to the capacitors (FIG. 2).

The substrate unit 50 is embedded within a unitary core 57. In one embodiment, the unitary core 57 may be formed having a uniform thickness around opposing major surfaces 53a, 53b of the substrate unit 50. As will be described with reference to FIGS. 7A-B, core 57 encapsulating the substrate unit 50 is formed by a molding process that utilizes a polymer bonded magnetic compound. Briefly, the molding process facilitates fabrication of custom dimensioned cores having package sizes that are smaller relative to those achievable with conventional cores. The packages may be molded having excess (sacrificial) material that facilitates handling during the various processing tasks, with the material being removed during a grinding process to obtain desired package dimensions.

FIGS. 5A to 5E depict cross-sectional views during tasks associated with a method for fabricating a transformer according to an embodiment of the disclosure such as that shown in FIGS. 3A and 3B. A substrate 44 (e.g., a printed wiring board or a semiconductor wafer) having a plurality of substrate units (e.g., 50a, 50b) is temporarily attached to a carrier plate 102. In the illustrative embodiment, the dotted line 100 demarcates the location where the substrate/wafer board 44 having a plurality of substrate units 50a-b would be sawed to separate the individual transformer units upon completion of the assembly. In one embodiment, the carrier plate 102 is made of stainless steel and has a thickness of, for example, between 2 and 10 mm. The shape and size of the carrier plate 102 may correspond to that of the substrate 44. The substrate 44 is attached to the carrier plate 102 using an adhesive layer 104 that has first and second opposing surfaces 106, 108, with a bottom surface 48 of the substrate being mounted to the first opposing surface and a surface 114 of the carrier plate being mounted to the second opposing surface. Although not specifically shown, the adhesive layer 104 may comprise a thermal release tape that includes thermally-degradable adhesive. Another example of the adhesive layer 104 may comprise a solvent-soluble adhesive, in which case, the carrier plate 102 is made of a porous material that allows a solvent to pass therethrough, such as a composite material of aluminum oxide embedded in a glass matrix.

In another embodiment, the substrate 44 may be attached to a single-sided PSA release tape that is not directly supported by a carrier plate. In the embodiment, the PSA release tape is suspended on a wafer mounting ring, and the substrate 44 is attached to the PSA release tape by vacuum lamination. Support for the PSA release tape and substrate is provided by a mold chase during molding.

The substrate 44 may comprise a standard G-10 board that is used for printed circuit boards, which include a copper conductor layer 51 etched on the bottom surface of the substrate. Other suitable materials for the substrate include metals, ceramics, plastics, polymers, and combinations thereof. The substrate 44 is formed having electronic components 52 that may be disposed on a top surface 46, or partially embedded, or fully embedded into the substrate material. In the simplest form, the electronic components 52 may comprise a set of windings, including both primary and secondary windings 59, 61. Each set of the primary and secondary windings 59, 61 may be coupled to terminal connectors 60 that are formed on the bottom (and/or top) surface 53b of each substrate unit horizontally-adjacent to the windings.

As is shown in the cross-sectional view, the electronic components 52 are arrayed to define depressions 68 that extend vertically, in relation to the top surface 53a, into the body of the substrate 44. The exemplary embodiment depicts the depressions 68 being arrayed in the form of an "E" 110. Although the illustrative embodiment depicts the depressions 68 being formed through the entire length of the body, it is contemplated that in other embodiments the depressions may alternatively be formed only partially into the body of the substrate.

FIG. 5B illustrates an upper core 56 that is placed over the top surface 53a of each of the substrate units 50. In the illustrative embodiment, the upper core 56 is an "E" core and legs 66 are disposed within the depressions 68 formed on the substrate unit 50. As such, the upper core 56 may be selected having dimensions that enable the upper core to be placed over the top surface 46 of the substrate 44. The dimensions of the legs 66 of the upper core 56 are also selected to fit within the depressions 68 of the substrate unit 50. In other embodiments, the converse relationship may be defined in the design criteria—i.e., the substrate unit 50 including the depressions 68 may be formed to match the dimensions of a pre-selected upper core. The upper core 56 may be a magnetic core formed from ferro-magnetic material, amorphous metal or other advanced materials as is known in the art.

Next, as illustrated in FIG. 5C, an encapsulant material 54 is dispensed (e.g., formed, injected, or deposited) over the top surface 46 of the substrate 44 and the exposed portions of the upper core 56 including the gaps between the upper core and the substrate. In one embodiment, the encapsulant material 54 may be deposited having a consistent cross-sectional area around the substrate/core assembly. For example, the encapsulant material 54 may be deposited to define a depth (or thickness) of, for example, approximately 1 mm around the substrate/core assembly. In one embodiment, the encapsulant material 54 is an electrically insulative material such as, a silica-filled epoxy, with a final cure temperature of, for example, between 140 and 150 degrees Centigrade (C). Other embodiments may use other types of encapsulant materials that have higher filler content or that are low modulus compounds. The carrier plate 102, along with the various components supported thereon, is subsequently heated or "baked" in, for example, an oven. In one embodiment, the baking is performed at a temperature of approximately 100 degrees C. for 60 minutes.

Figure 5D:
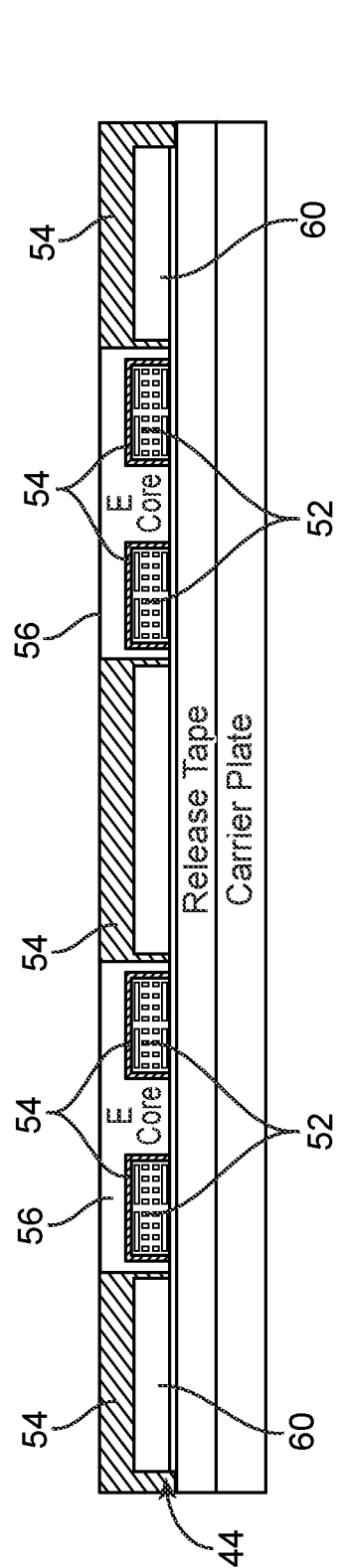

Subsequent to, at least partial, curing (e.g., 40% cure), the exposed encapsulant material 54 undergoes a grinding (and/or polishing, abrasion, milling) process to reduce the thickness of the molded assembly (encapsulant material and core) to a reduced, or thinned thickness as is shown in FIG. 5D. In other words, the molding process may include forming during the molding process a package that is larger than the desired final package to facilitate handling with the grinding process being performed to achieve the desired package dimensions. In the depicted embodiment, the grinding process is performed using a polishing or grinding head (or polishing element) that is placed into contact with and pressed against the molded assembly while being rotated and moved across the exposed surface of the assembly.

Figure 5E:
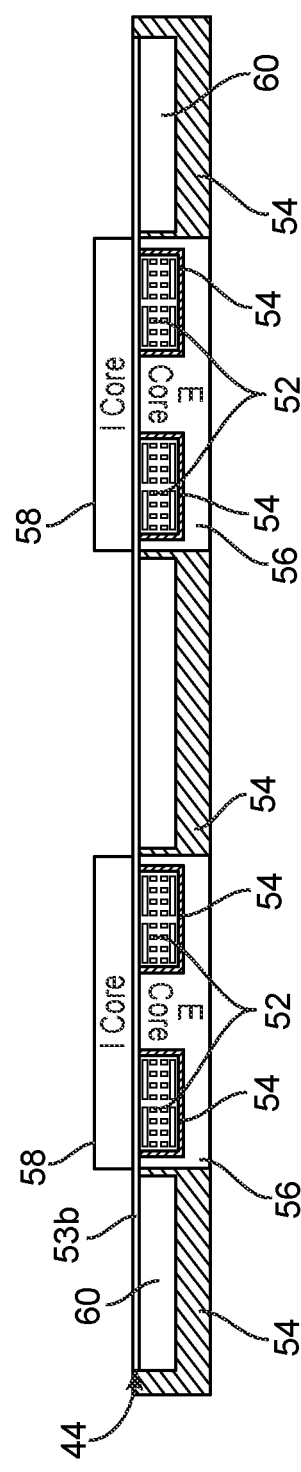

Turning next to FIG. 5E, the adhesive layer 104 is separated from the substrate 44 which in turn separates or unmounts the substrate from the carrier plate 102. The separation may be performed by, for example, exposing the adhesive to a solvent for a solvent-soluble adhesive, or heat, for a thermally degradable adhesive. Removal of the adhesive layer 104 exposes the terminals of the transformer assembly that are disposed on the bottom surface 53b of the substrate unit 50.

Additionally, a lower core 58 is attached to the bottom surface 53b of each of the substrate units 50. The lower core 58 is placed in an overlapping relation to the upper core 56 and away from the exposed terminals 60. The lower core 58 may be formed from materials similar to those of the upper core 56 including, but not limited to, magnetic materials. The lower core 58 may be configured, for example, as an "I" core element and may be selected having at least a lengthwise dimension that is matched with the length of the upper core 56. Without intending to be limiting, the fixation between the lower core 58 and the substrate unit 50 may be achieved through a pressure sensitive adhesive (PSA) compound. However, it should be noted that any other type of adhesion technique and/or adhesive compound may be utilized to achieve the bonding between the lower core 58 and the substrate unit 50a-b.

In embodiments in which the substrate 44 includes more than one substrate unit 50a-b, the substrate units are singulated along lines 100, for example, into individual units, such as those shown in FIGS. 3A and 3B. Singulation may be performed through, for example, sawing, or laser etching, or chemical singulation or any other methods known in the art.

Figure 6A:
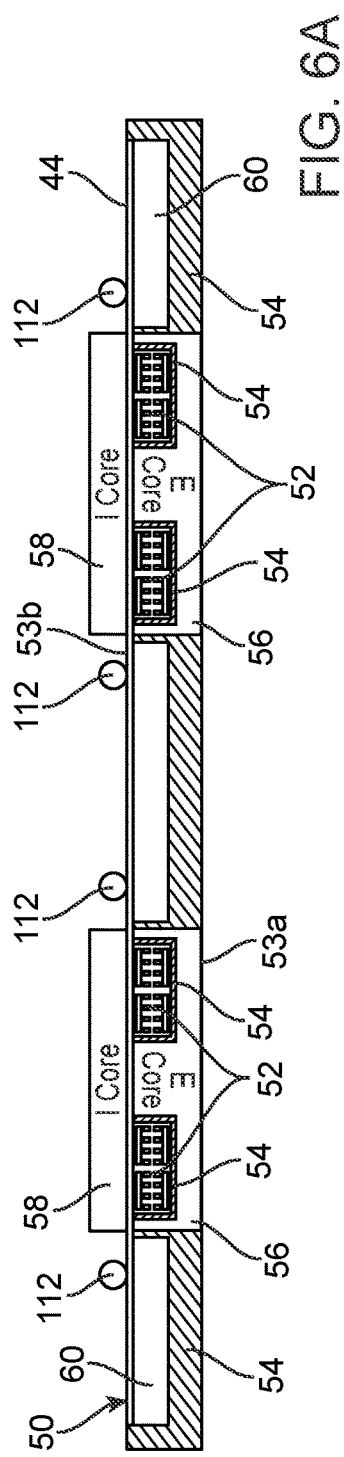
FIGS. 6A-6C depict cross-sectional views of a transformer assembly such as that shown in any one of FIGS. 3A and 3B associated with an alternative method for fabrication of the transformers.
Figure 6B:
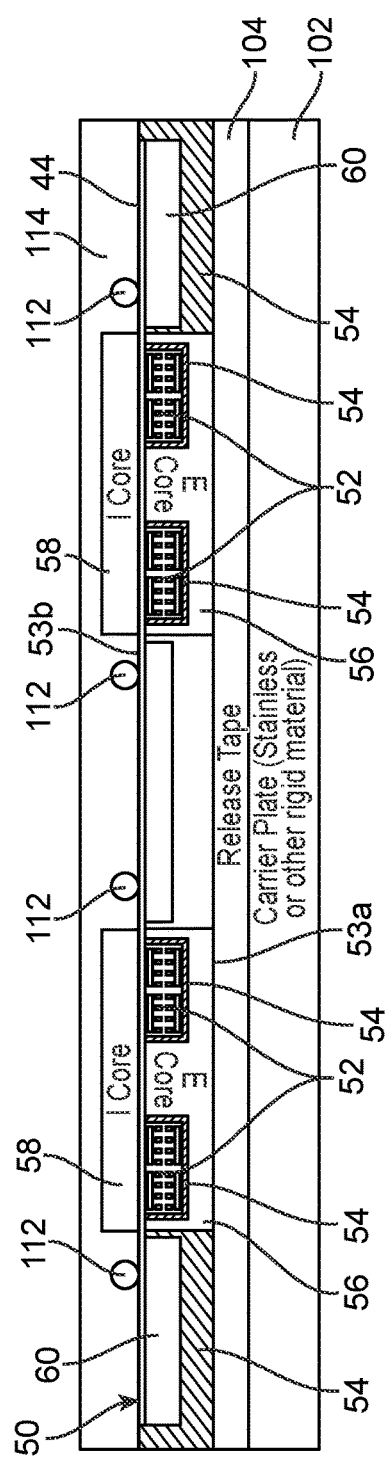
Figure 6C:
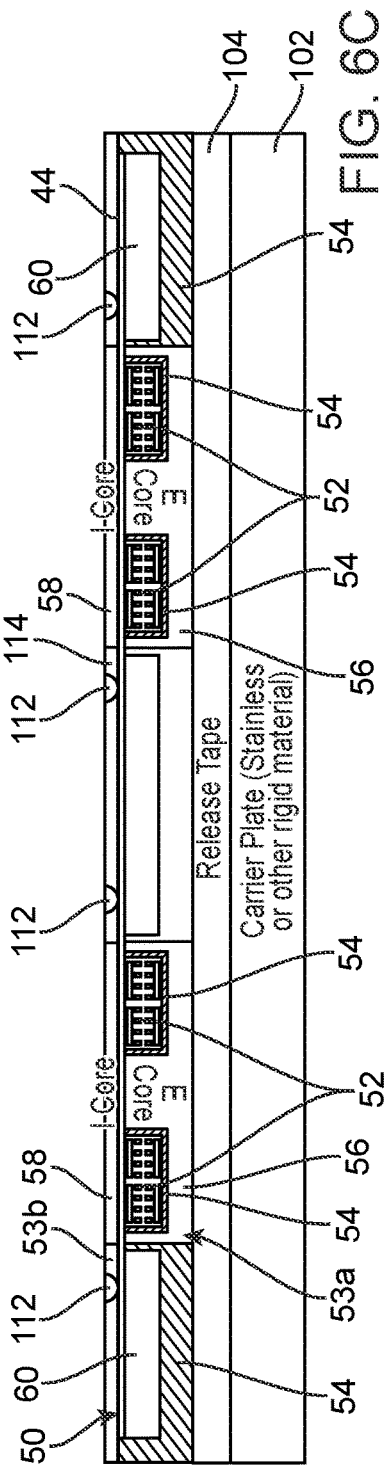

Turning to FIGS. 6A-6C, tasks for assembly of a transformer in accordance with an alternative embodiment are depicted. The tasks may be performed prior to the singulation of the substrate into individual substrate units. In FIG. 6A, a plurality of conductive pads 112 are connected to the substrate 44, such that one pad is coupled to each of the terminal connectors 60. The conductive pads 112 may be made of Aluminum (Al) or Copper (Cu) or any other conductive material with properties to enable soldering. In some embodiments, one or more surface mountable components, such as an integrated circuit (IC) (not shown), may also be coupled to the substrate unit's bottom surface 53b having electrical terminals for connection of the IC to other components of the IMD.

Next in FIG. 6B, a carrier plate 102 is attached to the top surface 53a of the molded substrate. An adhesive layer 104 may be used as described with reference to FIG. 5B to attach the carrier plate 102 to the top surface 53b. An encapsulant material 114, such as that described above, is subsequently dispensed over the bottom surface 53b of the substrate assembly, which includes the adhered lower core 58. In embodiments having the surface mountable component, the encapsulation of the bottom surface 53b is performed to also encapsulate such surface mountable components. Dispensing and curing of the encapsulant material 114 may be performed in accordance with the discussion above in conjunction with FIG. 5C.

Subsequently, after curing of the encapsulant material 114, the exposed encapsulant material 114 on the bottom surface 53b of the molded assembly undergoes a grinding (and/or polishing, abrasion, milling) process to reduce the thickness of the molded assembly (encapsulant material and core) to a reduced, or thinned thickness as is shown in FIG. 6C. The grinding also exposes the lower core 58 and the conductive pads 112 (and the IC terminals in embodiments having one or more ICs). In both grinding processes of FIGS. 6C and 5D, the lower and upper cores 58, 56 may also be thinned to a desired thickness, if appropriate. The top surface 53a is subsequently separated from the carrier plate 102 by detaching the adhesive layer 104.

Figure 7A:
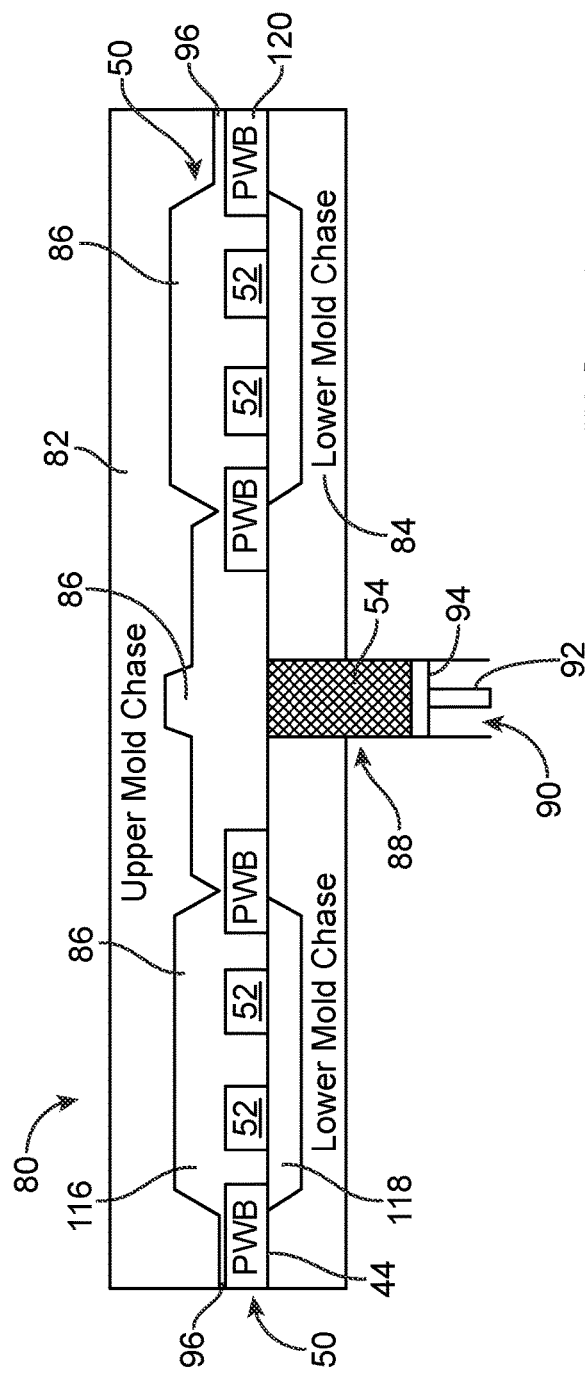
FIGS. 7A and 7B depict cross-sectional views of a transformer assembly such as that shown in any one of FIG. 4 associated with an alternative method for fabrication of the transformers.
Figure 7B:
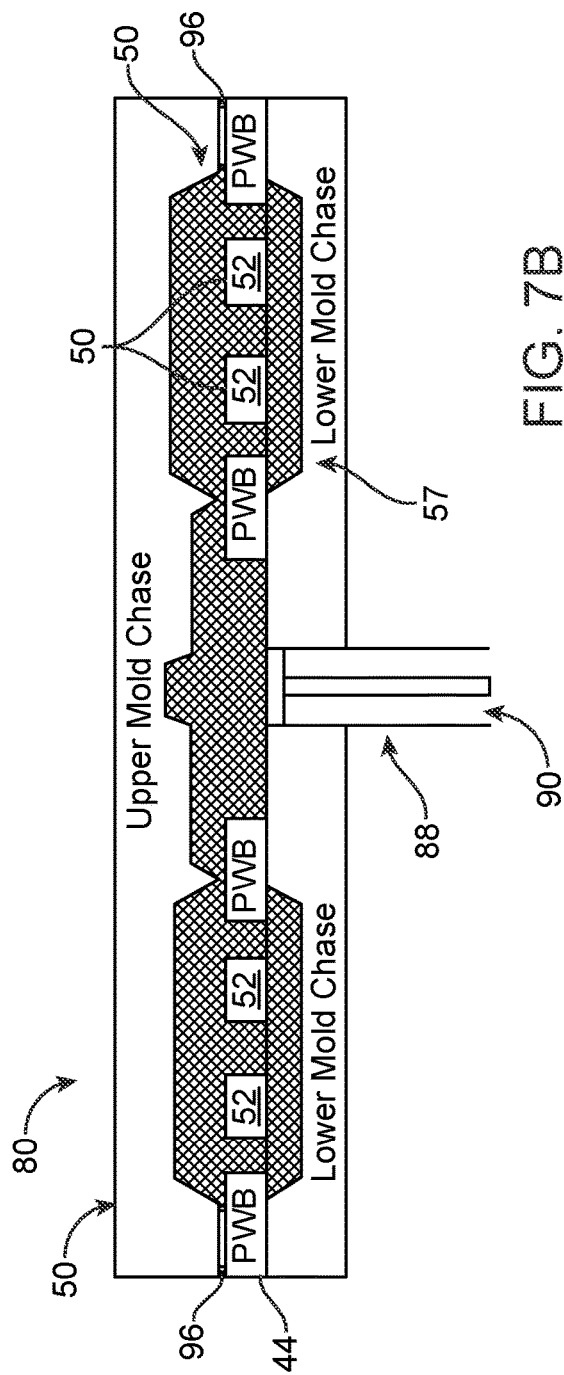

According to another embodiment of the present disclosure, another method for assembling a transformer, such as that depicted in FIG. 4, is disclosed which is illustrated in the FIG. 7A and FIG. 7B cross-sectional views of exemplary processing tasks. In this method, a homogeneous core 57 is integrally formed around a substrate unit 50 that includes a set of windings for the transformer. Unlike conventional transformer cores, the method of the embodiments described with reference to FIGS. 7A and 7B yield a homogenous transformer core 57 that can be custom-made with any desired shape or size and tailored to individual specifications and electrical performance characteristics.

Formation of the homogeneous core 57 to encapsulate the substrate unit 50 in accordance with embodiments of the method enables customization of the thickness of the core's sections on opposing surfaces of the substrate unit 50. For example, the thickness around opposing surfaces may be formed to be uneven based on desired electrical performance characteristics of the transformer. In yet another example, the core 57 may be formed by distributing the encapsulant material uniformly around the substrate unit to define a consistent cross-sectional area for the magnetic path.

As shown in FIG. 7A, a mold chase 80 is provided for formation of the core 57. The mold chase 80 includes an upper mold chase 82 having an upper cavity 116 and a lower mold chase 84 having a lower cavity 118. Upper mold chase 82 and lower mold chase 84 may be formed with corresponding cavity dimensions such that a continuous or contiguous central cavity 86 is formed when the upper mold chase 82 is placed over the lower mold chase 84. Additionally, each of the upper and lower cavities 116, 118 may be configured in a shape and size corresponding to that of a desired upper and lower core, respectively. Together, the upper and lower cavities 116, 118 define the central cavity 86 into which a substrate 44 having one or more substrate units 50 is received for encapsulation. Each substrate unit 50 or substrate 44 having a plurality of adjoining substrate units 50 is placed over the top surface 120 of the lower mold chase 84, with the upper mold chase 82 being separated from the lower mold chase 82. As discussed above, the substrate unit 50 is formed having one or more electronic components 52 that include a set of primary and secondary windings.

In one example, the mold chase 80 includes a receptacle 88 that is formed, for example, at a central portion of the lower mold chase 84. The receptacle 88 includes a hollow interior that is in fluid communication with a first opening at an outer surface of the lower mold chase 84 and a second opening into the lower cavity. A plunger 90 is disposed within the receptacle 88, and in use, the plunger 90 is moveable within the receptacle in a direction toward the second opening to transfer an encapsulant material 54 held within the receptacle 88 into the central cavity 86. As such, the plunger 90 may include a head plate 92 that is dimensioned to fit circumferentially-around a cylindrically-shaped receptacle, for example, with a pin 94 that is utilized for force transfer. The plunger 90 may be operated manually or under a hydraulic pressure.

The encapsulant material 54 may be held in the receptacle in a molten or liquefied state to facilitate the transfer from the receptacle into the central cavity 86 and to ensure complete encapsulation of the substrate units. Such encapsulation eliminates air gaps that may otherwise be formed between the substrate unit and the core.

The material selection for the encapsulant material is based on desired electrical functionality of the transformer and electrical properties of the core. Without intending to be limiting, the materials may include polymer bonded magnetic compounds formed, for example, by mixing a polymer binder with magnetic powder. The polymer binder can be either thermoplastic or thermoset. Thermoplastic polymer binders include Liquid Crystal Polymer (LCP), polyamine (e.g., Nylon 6), and polyphenylenesulfide (PPS) all of which are injection moldable materials. Thermoset binders can either be transfer molded or compression molded. Epoxy molding compounds are used in a transfer molding process while Phenolic and diallyl phthalate (DAP) resins can be used in a compression molding process. Soft magnetic powder can be Magnetics Molypermalloy Powder (MPP), soft ferrite, powdered iron, HI-FLUX, sendust, or Kool Mµ. Examples of polymer bonded magnetic compounds are commercially available from Arnold Magnetic Technologies Corporation of Rochester, NY.

Referring again to FIG. 7A, one or more outlet vents 96 are formed on the mold chase 80 to facilitate dispensing of the encapsulant material 54. In the illustrative embodiment, the dispensing of the encapsulant material 54 is performed in a transfer phase during which the encapsulant material 54 is expelled from the receptacle into the central cavity 86. The outlet vents 96 prevent a build-up of pressure inside the central cavity 86 that would otherwise create an opposing force that counteracts the flow of the encapsulant material into the cavity 86.

Turning next to FIG. 7B, the encapsulant material 54 is illustrated having being dispensed into the central cavity 86 for encapsulation of the substrate. The dispensing of the encapsulant material 54 into the cavity is performed while ensuring complete coverage of each substrate unit. This can be done by rapidly filling the central cavity 86, generally prior to initiation of the curing of the encapsulant material. In other embodiments, the encapsulant material 54 may be dispersed through a plurality of receptacles for even faster encapsulant filling. After the encapsulant material 54 is dispensed into the cavity 86, the molded assembly is cured.

The specifics pertaining to the curing of the encapsulant material cure will depend on the properties of the selected material. For example, the encapsulant material may cure fairly rapidly without any processing tasks in one embodiment. In other words, allowing the molded assembly to settle without more may permit the encapsulant material to be transformed into a solid state while it is held in the mold chase. In other embodiments, further processing tasks may be performed to enhance curing of the encapsulant material. For example, the mold chase may be cooled to a temperature that causes the encapsulant material to be transformed into a solid state, or the material may be heated to a temperature that causes the encapsulant material to harden (e.g., above 200° C.), or a chemical reaction may be performed, or the encapsulant material may be irradiated, or any other processing that causes the encapsulant material to harden based on its properties.

Subsequent to the curing cycle the molded assembly is ejected from the mold chase by separating the upper mold chase 82 from the lower mold chase 84. The molded assembly yielded includes one or more substrate units 50 encapsulated by an encapsulant material that becomes rigid to define the core 57, as illustrated in FIG. 4. Similar to the embodiments described in the figures above, the molded assembly may be formed having dimensions that are larger than the dimensions desired for a final package to facilitate handling. The molded assembly may further undergo a grinding (and/or polishing, abrasion) process to reduce the thickness of the core to a reduced, or thinned thickness. Further, in embodiments in which the substrate includes more than one substrate unit, the substrate units may be singulated to yield individual substrate units as shown in FIG. 4.

It should be noted that the description of the tasks in FIGS. 7A and 7B is merely exemplary of one molding process that can be used for forming a transformer assembly by encapsulating a substrate with an encapsulant material to yield a continuous high permeability magnetic path. Those skilled in the art will recognize that the principles described in the above tasks associated with a transfer molding process, may be embodied in other molding processes such as compression molding or injection molding depending on the polymer bonded magnetic compound.

Moreover, the foregoing assembly methods describe construction of planar transformer assemblies formed with a substrate having one or more sets of primary windings and secondary windings. The techniques described in the disclosure may, however, be suitably applied to assembly of non-planar transformers such as those having the primary and secondary windings that are wound on a bobbin.

The above description is intended to be illustrative, and not restrictive. For example, the above-described examples (or one or more aspects thereof) may be used in combination with each other. Other embodiments can be used, such as by one of ordinary skill in the art upon reviewing the above description. In the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method of forming a transformer assembly comprising:
   attaching a bottom surface of a substrate to a carrier plate, wherein the substrate comprises a plurality of substrate units, wherein a bottom surface of each substrate unit of the plurality of substrate units forms the bottom surface of the substrate;
   disposing electronic components on a top surface of the substrate or at least partially embedded in material of the top surface of the substrate, wherein at least one electronic component comprises primary and secondary windings, wherein a top surface of each substrate unit of the plurality of substrate units forms the top surface of the substrate;
   disposing an upper magnetic core over the top surface of each substrate unit of the plurality of substrate units and the electronic components;
   dispensing encapsulant material over the top surface of the substrate and exposed portions of the upper magnetic core and gaps between the upper core and the substrate to form a molded substrate;
   grinding portions of the encapsulant material and the upper magnetic core to form an upper planar surface of the molded substrate, wherein the upper planar surface comprises an exposed surface of the encapsulant material and an exposed surface of the upper magnetic core;
   removing the substrate from the carrier plate; and
   disposing a lower magnetic core to the bottom surface of each substrate unit of the plurality of substrate units.

2. The method of claim 1, further comprising disposing a second carrier plate on the upper planar surface of the molded substrate.

3. The method of claim 2, further comprising dispensing additional encapsulant material over the bottom surface of the substrate and the lower magnetic core.

4. The method of claim 3, further comprising at least partially curing the additional encapsulant material.

5. The method of claim 4, further comprising grinding the additional encapsulant material and the lower magnetic core to form a lower planar surface of the molded substrate, wherein the lower planar surface comprises an exposed surface of the additional encapsulant material and an exposed surface of the lower magnetic core.

6. The method of claim 5, wherein grinding portions of the additional encapsulant material and the lower magnetic core comprises thinning the lower magnetic core disposed on the bottom surface of each substrate unit to a desired thickness.

7. The method of claim 5, further comprising removing the second carrier plate from the upper planar surface of the molded substrate.

8. The method of claim 1, further comprising singulating the plurality of substrate units to provide individual substrate units.

9. The method of claim 1, further comprising at least partially curing the encapsulant material prior to grinding portions of encapsulant material and the upper core.

10. The method of claim 9, wherein at least one of the encapsulant material or additional encapsulant material comprises a polymer bonded magnetic material.

11. The method of claim 1, wherein attaching the bottom surface of the substrate to the carrier plate comprises attaching the bottom surface of the substrate to a first opposing surface of an adhesive layer and attaching a surface of the carrier plate to a second opposing surface of the adhesive layer.

12. The method of claim 11, wherein the adhesive layer comprises a thermal release tape comprising a thermally-degradable adhesive.

13. The method of claim 1, wherein disposing the lower magnetic core comprises adhering the lower magnetic core to the bottom surface of each substrate unit.

14. The method of claim 1, wherein grinding portions of the encapsulant material and the upper magnetic core comprises thinning the upper magnetic core disposed over the top surface of each substrate unit to a desired thickness.

15. The method of claim 1, further comprising forming one or more terminal connectors on at least one of the top surface or bottom surface of each substrate unit of the plurality of substrate units, wherein the primary and secondary windings of the at least one electronic component is coupled to a terminal connector of the one or more terminal connectors.

16. The method of claim 15, further comprising connecting a plurality of conductive pads to the substrate, wherein each terminal connector is coupled to a conductive pad of the plurality of conductive pads.

17. The method of claim 1, wherein at least one electronic component of each substrate unit of the plurality of substrate units comprises primary and secondary windings.

* * * * *